(12) United States Patent
Kahma

(10) Patent No.: US 8,133,693 B2
(45) Date of Patent: Mar. 13, 2012

(54) MEASUREMENT OF BINDING RATE OF A BINDING SUBSTANCE AND AN ANALYTE

(75) Inventor: Kauko Kahma, Espoo (FI)

(73) Assignee: Orion Diagnostica Oy, Espoo (FI)

( * ) Notice: Subject to any disclaimer, the term of this patent is extended or adjusted under 35 U.S.C. 154(b) by 695 days.

(21) Appl. No.: 11/919,728

(22) PCT Filed: May 5, 2006

(86) PCT No.: PCT/EP2006/004244
§ 371 (c)(1), (2), (4) Date: Jan. 14, 2009

(87) PCT Pub. No.: WO2006/119933
PCT Pub. Date: Nov. 16, 2006

(65) Prior Publication Data
US 2009/0215200 A1    Aug. 27, 2009

(30) Foreign Application Priority Data

May 9, 2005 (GB) .................................. 0509419.8

(51) Int. Cl.
*G01N 33/00* (2006.01)
(52) U.S. Cl. ........ 435/7.92; 435/7.1; 435/961; 436/501; 436/518
(58) Field of Classification Search ........................ None
See application file for complete search history.

(56) References Cited

U.S. PATENT DOCUMENTS

| | | | |
|---|---|---|---|
| 4,157,871 A | 6/1979 | Anderson et al. | |
| 4,204,837 A | 5/1980 | Sternberg et al. | |
| 4,205,954 A | 6/1980 | Babson | |
| 4,268,171 A | 5/1981 | Sternberg | |
| 4,575,485 A | 3/1986 | Sizto et al. | |
| 4,615,984 A | 10/1986 | Stoker | |
| 4,766,083 A | 8/1988 | Miyashita et al. | |
| 4,826,319 A | 5/1989 | Namba et al. | |
| 4,835,110 A | 5/1989 | Seymour et al. | |
| 5,227,312 A | 7/1993 | Grundy | |
| 5,371,021 A | 12/1994 | Oh et al. | |
| 5,527,710 A * | 6/1996 | Nacamulli et al. | 436/517 |
| 5,583,055 A | 12/1996 | Oh et al. | |
| 5,665,605 A | 9/1997 | Coakley et al. | |
| 5,853,994 A | 12/1998 | Gopinathan et al. | |
| 5,912,182 A | 6/1999 | Coakley et al. | |
| 5,989,806 A * | 11/1999 | Brust | 435/5 |
| 6,086,821 A | 7/2000 | Lee | |
| 6,368,553 B1 | 4/2002 | Lee | |
| 7,183,119 B2 * | 2/2007 | Qiao et al. | 436/518 |
| 7,373,255 B2 * | 5/2008 | Karlsson et al. | 702/19 |
| 2003/0143565 A1 * | 7/2003 | Trutnau | 435/6 |
| 2004/0265871 A1 | 12/2004 | Angelsen et al. | |

FOREIGN PATENT DOCUMENTS

| | | |
|---|---|---|
| EP | 0 137 678 A | 4/1985 |
| EP | 0414223 | 2/1991 |
| GB | 2233089 A | 1/1991 |
| WO | 99/14599 WO | 3/1999 |

OTHER PUBLICATIONS

Ellis, Richard et al, "Diagnostic particle agglutination using ultrasound: a new technology to rejuvenate old microbiological methods," J. Med. Microbiol., 49 853 (2000).
Haga et al., "Effect of Ultrasonic Irradiation on the Dissociation of Antigen-Antibody Complexes. Application to Homogenous Enzyme Immunoassay," Chem. Pharm. Bull., 35 3822 (1987).
Australian Office Action regarding Application No. 2006246008, dated Nov. 19, 2010.
Chinese Office Action regarding Application No. 200680015934.6, dated Oct. 28, 2010. Translation provided by Orion Corporation.
European Office Action regarding application 06 724 740.3-1223, dated May 15, 2008.

* cited by examiner

*Primary Examiner* — Bao Thuy L Nguyen
*Assistant Examiner* — Gary W Counts
(74) *Attorney, Agent, or Firm* — Harness, Dickey & Pierce, P.L.C.

(57) ABSTRACT

A method of measuring the rate of binding of a binding substance and an analyte, for example in an assay such as an immunoassay, uses an initial step of performing ultrasonication sufficient to disrupt binding between the binding substance and the analyte. After cessation of the ultrasonication, measurements are taken to determine the rate of binding at cessation of said ultrasonication or at a predetermined time thereafter. The ultrasonication results in knowledge of the precise time of the start of the binding reaction which provides a better rate measurement.

26 Claims, 1 Drawing Sheet

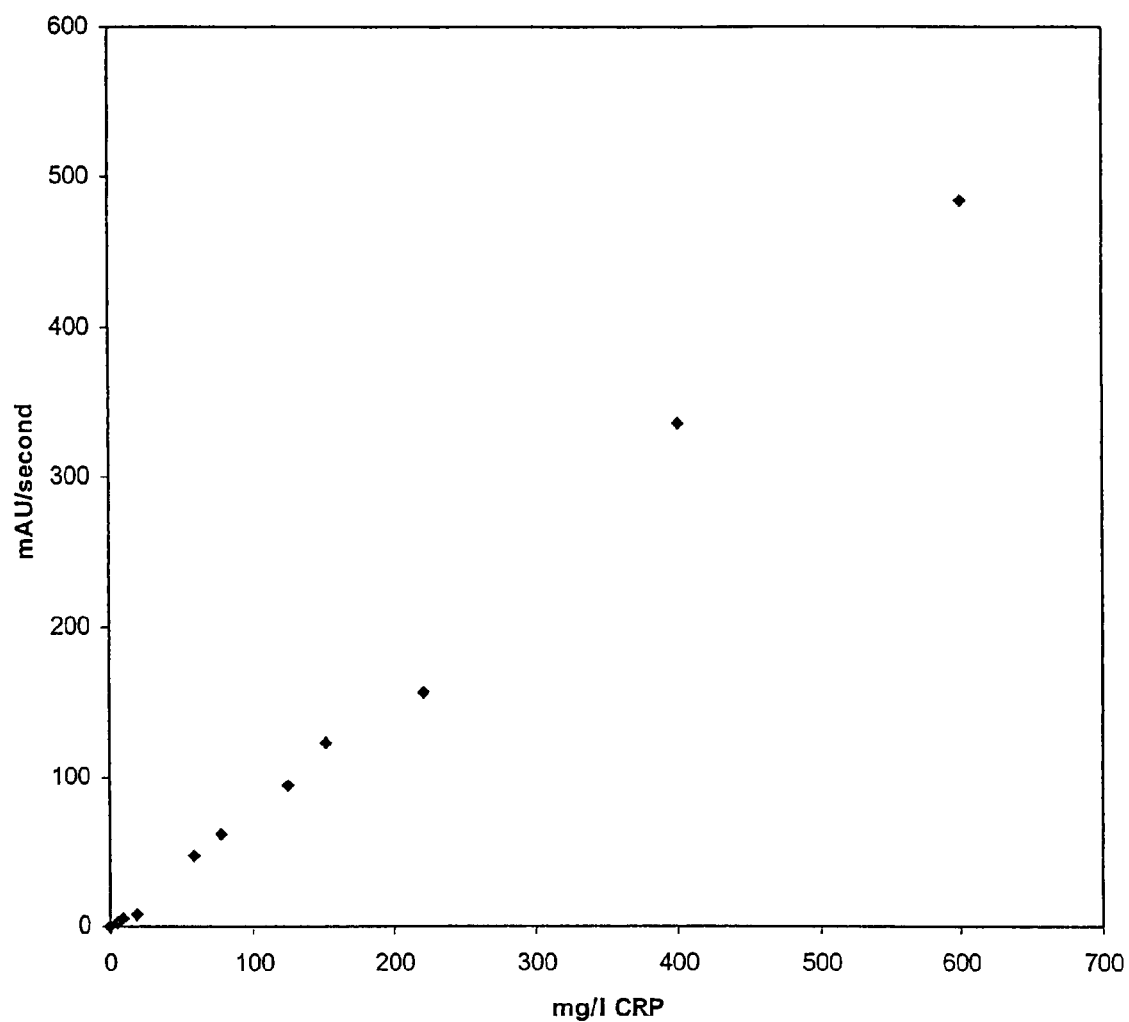

stop.

MEASUREMENT OF BINDING RATE OF A BINDING SUBSTANCE AND AN ANALYTE

CROSS-REFERENCE TO RELATED APPLICATIONS

This Application is a National Stage of International Application No. PCT/EP2006/004244, filed May 5, 2006. This application claims the benefit of GB 0509419.8, filed May 9, 2005. The disclosure(s) of the above applications are incorporated herein by reference.

FIELD

The present invention relates to a method of measuring the rate of binding of a binding substance and analyte, for example in an assay such as an immunoassay. The measured rate of binding may be useful, for example, in deriving the concentration, amount or presence of the analyte.

BACKGROUND

Existing immunoassay methods involving measurement of binding rate suffer from the problem that the exact time when the reaction actually starts cannot be known because of practical difficulties in mixing. This limits accurate determination of initial binding rates. Thus typically a constant initial rate of reaction is required. For example, methods utilizing constant initial rate have been described in U.S. Pat. Nos. 4,205,954, 5,371,021 and 5,583,055. In another type of method, the peak binding rate is measured, for example as described in U.S. Pat. Nos. 4,157,871, 4,204,837, 4,268,171, 4,766,083 and 4,835,110.

A disadvantage of these methods is the relatively long time needed to gather enough information from the reaction in order to be able to determine the concentration of the sample. A further disadvantage is the need to start the actual measurement immediately after the addition of the sample.

SUMMARY

This section provides a general summary of the disclosure, and is not a comprehensive disclosure of its full scope or all of its features.

The present teachings provide for a method of measuring the rate of binding of a binding substance and an analyte. The method includes disposing the binding substance and the analyte in a medium, performing sonication of the medium sufficient to disrupt binding between the binding substance and the analyte, and ceasing said sonication of the medium and determining the rate of binding at a predetermined time at or after cessation of said sonication by extrapolation from measurements made after cessation of said sonication.

Further areas of applicability will become apparent from the description provided herein. The description and specific examples in this summary are intended for purposes of illustration only and are not intended to limit the scope of the present disclosure.

DRAWING

The drawing described herein is for illustrative purposes only of selected embodiments and not all possible implementations, and is not intended to limit the scope of the present disclosure.

FIG. 1 is a graph of a calibration curve according to the present teachings.

DETAILED DESCRIPTION

Example embodiments will now be described more fully with reference to the accompanying drawing.

According to the present invention, there is provided a method of measuring the rate of binding of a binding substance and an analyte, by performing sonication of the binding substance and the analyte in a medium so as to disrupt binding between the binding substance and the analyte, ceasing the sonication and determining the rate of binding at cessation of said sonication or a predetermined time thereafter.

The method may be used to derive the concentration, amount or presence of the analyte from the determined binding rate, for example as an assay or immunoassay. The sonication, typically ultrasonication in the form of a short pulse, disrupts the binding and effectively resets the binding reaction to a known initial condition. For example where the binding complex agglutinates, the agglutination may visibly reduce or disappear. The binding reaction commences on cessation of the sonication. The point in time when this occurs is accurately known and this makes it possible to determine the initial rate of binding in an accurate manner. Usually the determined binding rate is the rate at the actual cessation of the sonication, but it may in some cases be a predetermined time thereafter.

As a result, the method is faster than conventional methods as well as being more reliable and sensitive. It may use only one reagent. It may also use the homogenous immunoassay principle with no need to separate bound and unbound ligands. The analyte, e.g. a blood sample or a standard, can be added to the medium prior to performing the method, because the sonication will disrupt the binding or agglutination that happens prior to the actual measurement. It is a further advantage of the invention that the possible non-specific aggregation of the reagent during storage can be effectively disrupted by the same sonication step used for the assay.

According to the invention, there is no need for the reaction rate to be linear, because the reaction start time is known exactly, so that there is no need to use the more cumbersome methods described in prior art.

Advantageously, the binding rate may be determined by making measurements at a plurality of times after cessation of said sonication and deriving the rate of binding at said predetermined time by extrapolation from the measurements.

The extrapolation may be performed, for example, by fitting a curve to the measurements and calculating the rate of binding at said predetermined time from the fitted curve. Alternatively a more complicated form of extrapolation may be performed. In one example, an initial estimate of the rate of binding at said predetermined time is calculated from a first curve fitted to the data and used to determine a curve fitting algorithm. Then, a second curve is fitted to the measurements using the determined curve fitting algorithm and the rate of binding at said predetermined time is determined from the fitted curve.

However the binding rate may be calculated in other ways. For example, an alternative is to apply a technique in which a property is measured at two points in time and the difference is taken as being representative of the binding rate. In this case, although the difference is not in the correct units it is representative of the rate because the interval between the measurements is fixed. For example, if the measurements are representative of the amount of at least one of the binding substance, analyte or the bound complex of the binding substance, the difference is proportional to the rate, the actual rate equals the difference divided by the interval between the measurements. The terms "rate of binding" and "binding rate" are used in this application to cover such techniques in which there is calculated a value representative of the rate even if not in proper units. However this alternative technique is not preferred as it results in a value representative of the average rate over the interval, rather than the rate at the actual cessation of sonication.

The measurements may be measurements representative of the amount of at least one of the binding substance, analyte or the bound complex of the binding substance and the analyte, typically being optical measurements, using for example but not exclusively turbidometry, nephelometry or fluorometry. In general, the rate of binding may be determined photometrically, as for example in known binding rate photometric immunoassay methods, or in any other way.

One optional technique is to perform, prior to adding a sample containing the analyte to the binding substance contained in a medium, sonication of the same nature as subsequently performed to disrupt the binding and to take a preliminary measurement. Then, the preliminary measurement may be subtracted from each of the measurements made after cessation of said sonication, or may be extracted from the extrapolated value of the measurement at the predetermined time. Thus the net value of the measured property is obtained. This opens up the possibility of measuring a constant property of the sample by subtracting the preliminary measurement taken from the binding substance in the absence of the sample. This allows the measurement of a property, for example the absorbance of the sample or another optical property, without the disturbance of the ongoing reaction which also affects the property. Knowledge of the value of the property can be used for example for the measurement of the haemoglobin content and haematocrit of a blood sample.

An alternative way to achieve this is to extrapolate the measurements back to the time of cessation of the sonication. In many practical situations, this alternative technique is the only effective way to measure the property without disturbing the ongoing reaction. In those cases, this can only be done by first measuring the property of the sample in buffer and then adding a second reagent to start the reaction. Avoidance of such a complicated procedure is another advantage of the sonication in the present invention.

The method is generally applicable to any type of binding which is capable of being disrupted by sonication. Specific and possibly non-specific binding between the particles may be disrupted. Typically the binding is reversible, non-covalent binding. Typically one or both of the binding substance and the analyte is a protein. The method is applicable to binding between two or more entities.

The method has particular application to immunological binding. In this case, the binding substance may be an antibody, an antigen (protein or non-protein) or a hapten. As used herein the term "antibody" includes fragments which bind to an analyte. Such fragments include Fv, F(ab') and F(ab')$_2$ fragments. Furthermore the antibody or fragment may be a chimeric antibody, a CDR antibody or a humanised antibody.

An alternative is to apply the method to binding between a receptor and a ligand.

The binding substance and the analyte may be disposed in the medium in any suitable form. One possibility is to simply suspend both the binding substance and the analyte in the medium, for example with the binding substance coated on insoluble carrier particles. However, other more complicated techniques may equally be applied.

The present method may be applied to analyze analytes from a wide range of samples including both clinical and non-clinical samples such as hygiene samples. Samples from different body fluids such as whole blood, serum, plasma, spinal fluid, ascites fluid, urine, saliva, semen and samples for hygiene monitoring such as food, milk, sterility control swipes from surfaces or water can be used.

Usually the analyte is determined from the sample without any additional processing, however, if needed, the sample may be pre-treated prior to the assay, eg centrifuged, haemolysed or enriched.

Sonication is the application of sound waves (audible sound or ultrasound) to the medium. Many types of apparatus for performing sonication are known and any type of sonication apparatus can be used because the method is not dependent on the nature of the apparatus itself. One non-limitative example is to use the sonication apparatus described in the International Patent Application being filed simultaneously with this application entitled "Sonication Of A Medium" (claiming priority from British Patent Application No. 0509418.0), which is incorporated herein by reference.

The frequency of the sonication can be selected from a wide range of frequencies. The dissociative energy increases as the frequency increases so enabling a wide choice of disruptive forces to be used for any practical application. The choice of frequency and power may be made for any given binding by simple trial of different frequencies and powers to select a frequency and power providing the necessary disruption of the binding. Usually the frequency is at least 1 kHz, but more typically the frequency is at least 20 kHz in which case the sonication may be termed ultrasonication. Usually the frequency is at most 1000 kHz. The sonication is applied for a period sufficiently long to disrupt the binding, this typically being of the order of seconds.

There are some known techniques using ultrasound in immunoassays but in a different manner from the present invention. Some of the known uses of ultrasound are as follows.

It is known that ultrasound can be used to enhance coated particle agglutination immunoassays by using a ultrasonic standing wave field. A large amount of reports were published from the mid-1980s to the late 1990s, wherein ultrasound was used to enhance both rate and sensitivity of an agglutination assay. Such documents disclose only ultrasound-enhanced agglutination, whereas none of the publications in this group report usage of ultrasound to disrupt specific ligand anti-ligand bonds. Examples of documents disclosing such ultrasonic enhancement of agglutination are GB-A-2,233,089, U.S. Pat. Nos. 4,575,485, 5,227,312, 5,665,605, 5,853,994, 5,912,182 and Ellis et al. "Diagnostic particle agglutination using ultrasound: a new technology to rejuvenate old microbiological methods" J. Med. Microbiol. 49 853 (2000). In the present invention, the sonication disrupts the binding which is the opposite effect from enhancing or driving the binding reaction. However, such use of ultrasound to enhance the reaction may be used in the present method by performing the enhancing ultrasonication (typically a sufficiently low energy ultrasound of a suitable frequency) after cessation of the sonication which disrupts the binding, if such enhancement should be needed.

The following publications describe the use of ultrasound for disrupting ligand anti-ligand bonds. In U.S. Pat. No. 4,615,984 and Haga et al. "Effect of Ultrasonic Irradiation on the Dissociation of Antigen-Antibody Complexes. Application to Homogenous Enzyme Immunoassay" Chem. Pharm. Bull. 35 3822 (1987) ultrasound is used for dissociating ligand-binder complex permitting the reuse of the binder.

Reuse of the binder takes place in a separate assay. In U.S. Pat. No. 6,086,821 ultrasonic force is used to dissociate antigen-antibody complexes in order to measure binding affinities between antigen and antibody, however no measurement of reaction rate is described or claimed nor is the invention used for concentration measurement of an analyte. In U.S. Pat. No. 6,368,553 an assay device is described that uses ultrasonic force to dissociate antigen-antibody complexes in order to detect analytes in the presence of a•abelled reagent, however no measurement of reaction rate is described or claimed.

The method makes possible a very rapid quantitative measurement, because the initial reaction rate can be calculated after only a few seconds (typically 0.5-30 sec.) measurement of the rate curve. Preferably, the measurement takes 1-15 seconds, or even more preferably 1-10 seconds. Of course in principle the reaction can be followed for as long as is needed for gathering sufficient data for needed accuracy, even tens of minutes.

Furthermore, the measurement can be repeated if needed for improved accuracy by repeating the sonication and measuring the initial rate again.

A non-limitative example of the present method will now be described with reference to the drawings, in which:

FIG. 1 is a graph of the calibration curve for the example.

The method was performed in respect of CRP antibodies as the binding substance and CRP as the analyte.

Latex particles coated with CRP antibodies were obtained from QUIKREAD CRP kit (Cat. no. 67961) manufactured by Orion Diagnostica Oy, Finland. The coating of latex particles was performed in the manner described in EP-A-0,946,871. The concentration of latex particles was adjusted to 2 g/l with 0.15 mol/l pH 8.4 tris(hydroxymethyl)aminomethane-HCl buffer containing 0.171 mol/l NaCl and 0.1% bovine serum albumin.

A series of CRP standard solutions having concentrations of 0, 5, 9, 19, 59, 78, 15 125, 151, 221, 400 and 600 mg/l was prepared. The following procedure was carried out for each of the standard solutions.

1 ml of latex suspension in buffer was pipetted in a cuvette, and 12 µl of standard was added.

The ultrasonication was performed using a method and apparatus described in the International Patent Application being filed simultaneously with this application entitled "Sonication Of A Medium" (claiming priority from British Patent Application No. 0509418.0), which is incorporated herein by reference. This enabled a simple construction and a rapid procedure. Furthermore, the cuvette can be completely closed during ultrasonication which prevents the spread of possibly infective or otherwise harmful material from the cuvette during ultrasonication.

Next the cuvette was positioned between the fork-shaped ultrasonicating head positioned within a photometer. The ultrasonicating head contacted directly the cuvette from both sides, but did not obstruct the photometer light path. The photometer was set to record the absorbance at 653 nm three times per second and the measurement was started.

Next, the cuvette was ultrasonicated for 6 seconds with a sonication frequency of 37 kHz and the agglutination reaction was let to proceed after the ultrasonication for one 5 minute. As the ultrasonication stops, the agglutination reaction immediately starts. The moment at the end of the ultrasonication was defined as zero time.

Next, the absorbance readings of each of the experiments were plotted with absorbance on y-axis and time on x-axis. A second degree polynomial of the form $y=ax^2+bx+c$ was fitted via the experimental points starting from ⅔ seconds after the end of the sonication and ending at three seconds after the end of the sonication. The value of the first derivative ($y=2ax+b$) of the second degree polynomial calculated at zero time is the initial reaction rate of the agglutination reaction. The obtained initial reaction rates of each of the standards expressed as absorbance units per second were plotted as a calibration curve which is shown in FIG. 1. This calibration curve was linear from 5 mg/l 15 up to 600 mg/l.

In general, any mathematical function could be fitted to the rate curve. The initial reaction rate at the time when the ultrasonication stops or a predetermined time thereafter may be calculated by calculating the value of the first derivative of the mathematical function at the appropriate time.

The invention claimed is:

1. A method of measuring the rate of binding of a binding substance and an analyte, the method comprising:
    disposing the binding substance and the analyte in a medium;
    performing sonication of the medium sufficient to disrupt binding between the binding substance and the analyte; and
    ceasing said sonication of the medium and determining the rate of binding at a predetermined time at or after cessation of said sonication by extrapolation from measurements made after cessation of said sonication.

2. The method according to claim 1, wherein said step of determining the rate of binding comprises: making measurements at a plurality of times after cessation of said sonication; and deriving the rate of binding at said predetermined time by extrapolation from the measurements.

3. The method according to claim 2, wherein said step of deriving the rate of binding at said predetermined time by extrapolation comprises: fitting a curve to the measurements; and calculating the rate of binding at said predetermined time from the fitted curve.

4. The method according to claim 2, wherein said step of deriving the rate of binding at said predetermined time by extrapolation comprises: fitting a first curve to the measurements; calculating an initial estimate of the rate of binding at said predetermined time from the fitted first curve; determining a curve fitting algorithm from said initial estimate of the rate of binding at said predetermined time; fitting a second curve to the measurements using the determined curve fitting algorithm; and calculating the rate of binding at said predetermined time from the fitted second curve.

5. The method according to claim 2, wherein said plurality of times are within 30 seconds from cessation of said sonication.

6. The method according to claim 1, wherein said step of determining the rate of binding comprises: making a first measurement at or after cessation of said sonication and a second measurement at a predetermined interval after the first measurement; and taking the difference between the first and second measurements as the determined rate of binding.

7. The method according to claim 2, wherein said measurements are measurements of a quantity representative of the amount of at least one of the binding substance, analyte or the bound complex of the binding substance and the analyte.

8. The method according to claim 7, wherein said measurements are performed optically.

9. The method according to claim 8, wherein said measurements are measurements of absorption of light by the medium, of light scattered by the medium or of fluorescence from the medium.

10. The method according to claim 7, further comprising determining the value of said quantity at cessation of said sonication by extrapolation from the measurements.

11. The method according to claim 7, wherein: said step of disposing the binding substance and the analyte in a medium comprises adding a sample containing the analyte to the binding substance contained in a medium; said method further comprises, prior to adding the sample containing the analyte to the binding substance, performing said sonication and making a preliminary said measurement.

12. The method according to claim 1, wherein said step of determining the rate of binding is performed photometrically.

13. The method according to claim 1, wherein the binding is immunological binding.

14. The method according to claim 13, wherein the binding substance is an antibody, an antigen or a hapten.

15. The method according to any claim 1, wherein one of the binding substance and the analyte is a receptor and the other of the binding substance and the analyte is a ligand.

16. The method according to claim 1, wherein the binding is non-covalent.

17. The method according to claim 1, wherein the binding substance is coated on insoluble carrier particles.

18. The method according to claim 1, wherein said sonication is performed at a frequency of at least 1 kHz.

19. The method according to claim 1, wherein said sonication is performed at a frequency of at least 20 kHz.

20. The method according to claim 1, wherein said sonication is performed at a frequency of at most 1000 kHz.

21. The method according to claim 1, further comprising, after cessation of said sonication of the medium sufficient to disrupt binding between the binding substance and the analyte, performing sonication capable of enhancing binding between the binding substance and the analyte.

22. The method according to claim 1, wherein said predetermined time is at the cessation of said sonication.

23. The method according to claim 1, further comprising determining the amount, concentration or presence of the analyte from the determined rate of binding.

24. The method according to claim 1, further comprising repeating said steps of performing sonication of the medium and determining the rate of binding at a predetermined time; and averaging the repeatedly determined rates of binding.

25. The method according to claim 2, wherein said step of deriving the rate of binding by extrapolation from the measurements further comprises calculating the rate of binding at zero time.

26. The method according to claim 3, wherein said step of deriving the rate of binding by extrapolation from the measurements further comprises:
    fitting a curve to the measurements; and
    calculating the rate of binding at zero time from the fitted curve.

* * * * *